United States Patent [19]

Gottschalk

[11] Patent Number: 5,085,209
[45] Date of Patent: Feb. 4, 1992

[54] PENILE ERECTION ENHANCING COLLAR AND METHOD

[76] Inventor: G. Howard Gottschalk, 8618 Sepulveda, Los Angeles, Calif. 90045

[21] Appl. No.: 322,625

[22] Filed: Mar. 13, 1989

[51] Int. Cl.⁵ .............................................. A61F 5/41
[52] U.S. Cl. .................................... 600/41; 606/201
[58] Field of Search ............... 128/876, 883, 885, 157, 128/79, 325-327, DIG. 25; 606/201

[56] References Cited

U.S. PATENT DOCUMENTS

| | | | |
|---|---|---|---|
| 678,943 | 7/1901 | Davis | 128/885 X |
| 1,810,027 | 6/1931 | Moran et al. | 128/327 |
| 2,581,114 | 1/1952 | Larson | 128/327 |
| 3,155,096 | 11/1964 | Outwin | 128/327 |
| 3,461,863 | 8/1969 | Sullinger | 128/327 |
| 3,633,572 | 1/1972 | Wiggins | 128/79 |
| 3,636,948 | 1/1972 | Atchley | 128/79 |
| 3,773,040 | 11/1973 | Gavrilovich | 128/79 |
| 3,799,157 | 3/1974 | McIntire | 128/79 |
| 3,845,761 | 11/1974 | Birman | 128/327 X |
| 4,273,130 | 6/1981 | Simpson | 128/327 |
| 4,760,846 | 8/1988 | Mers Kelly et al. | 128/327 |
| 4,773,419 | 9/1988 | Tountas | 128/327 |

FOREIGN PATENT DOCUMENTS

| | | | |
|---|---|---|---|
| 910206 | 3/1954 | Fed. Rep. of Germany | 128/79 |
| 122185 | 9/1927 | Switzerland | 128/325 |
| 235628 | 6/1925 | United Kingdom | 128/327 |

*Primary Examiner*—Robert A. Hafer
*Assistant Examiner*—Kevin G. Kooney
*Attorney, Agent, or Firm*—Lyon & Lyon

[57] ABSTRACT

A therapeutic, sanitary device intended to promote satisfactory sexual intercourse by preventing impotency, and a method of maintaining erection of the penis by use of said device, is disclosed. The device consists of a band of interlocking material being at least of a length sufficient to both encircle the base of a penis and scrotum at the junction of the pubis and to interconnect against itself when so encircled. A self-enclosed circular region attached to an end of said device to act as a "noose" is further described, whereby said device may be pulled tightly against itself in an effort to be cinched tightly against said junction.

16 Claims, 3 Drawing Sheets

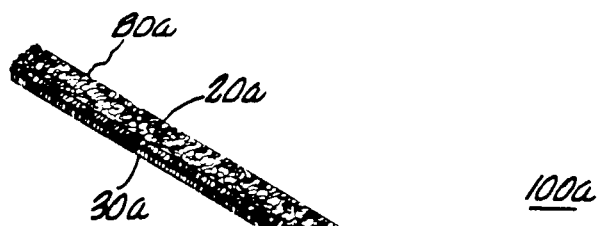
FIG._1_
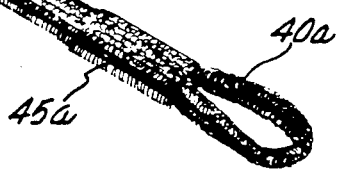
FIG._2_
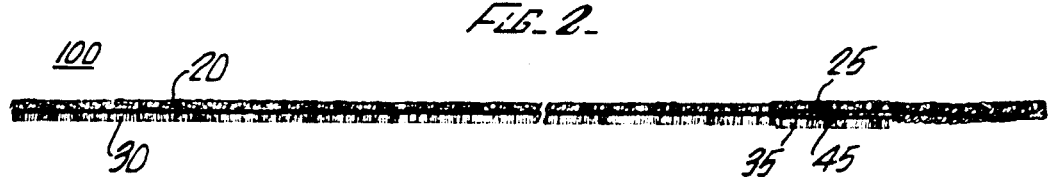
FIG._3_
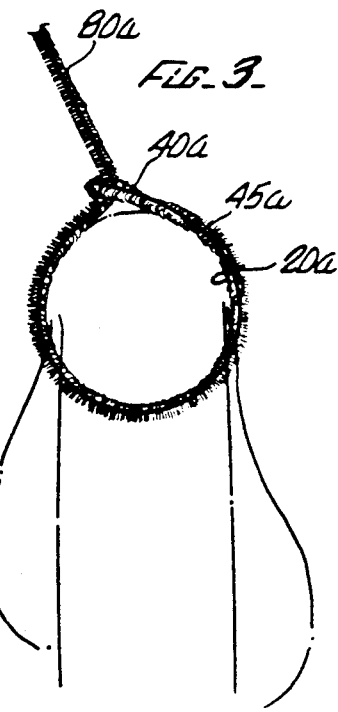
FIG._4_
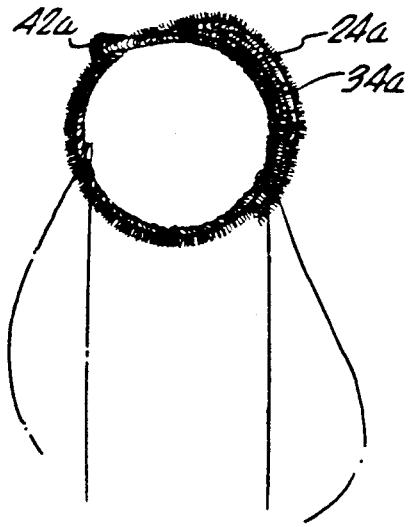

PENILE ERECTION ENHANCING COLLAR AND METHOD

BACKGROUND OF THE INVENTION

The present invention relates to a new, useful and sanitary device intended to promote satisfactory sexual intercourse by assisting to maintain the penis in an erect state during intercourse while both preventing the problems associated with impotency and avoiding the need for large, bulky and embarrassingly awkward erection-maintaining devices.

DESCRIPTION OF RELATED ART

Publications and other materials used to illuminate the Background, Summary and Detailed Description of the Invention are incorporated herein by reference.

Impotency can be caused by a variety of physical and/or psychological reasons. Irrespective of the reasons for this devastating problem, the frustration and embarrassment felt by those who suffer from impotency can be compounded by utilization of devices which attempt to prevent the problem, yet merely serve to highlight the problem. Additionally, such devices are usually large, and therefore designed for repeated use, thus raising the spectre of disease caused by a re-usable, unsanitary device. It is to this dual problem that the present invention is directed.

Erection of the penis occurs under sexual stimulation which causes a highly increased blood flow through the corpora cavernosa. As long as this condition prevails, the erection is maintained. The state of erection, however, is not maintained in some individuals long enough to complete copulation satisfactorily for both partners. This condition can be remedied by restricting the outflow of blood from the corpora cavernosa and thus maintaining the erection. However, merely preventing the flow of blood from the corpora cavernosa, but not taking into account the embarrassment caused by using devices which serve as a vivid reminder of the individuals impotency, accentuates the problem. Clearly, subtlety of the device is as important as the biological objective of the device.

In U.S. Pat. No. 3,633,572, a Copulation-Assisting Device is described whereby an elastic loop having a cushioned sleeve partially covers the penis such that the penial shaft is encircled around the top and both sides thereof, while the underside of the shaft containing the urethra is left relatively free. An elastic band extends through the cushioned sleeve and forms a single strand, the end of which incorporates a fastener which is engaged with apertures so as to vary the tension of the elastic loop around the penis. The device is fastened in position by either applying adhesion tape (attached to the fastener portion of the device) to the gluteal region of the user, such as one of the buttocks, or by wrapping the strand around the users leg. Reference is also made to U.S. Pat. No. 3,799,157 wherein a first penis-encircling band and a second scrotum-encircling band form interconnected loops is described, such that the first band fits snugly around the base of the penis, while the second band fits extended around the neck of the scrotum.

These devices, while preventing the flow of blood from the penis, are unavoidably awkward for the user and merely highlight the problem to which they are directed. Additionally, these devices are not disposable, but are intended for repeated use. Since impotency in and of itself creates feelings of inferiority and embarrassment, a device to correct this problem should avoid, at all costs, casting a spotlighting on the problem.

SUMMARY OF THE INVENTION

As such, the principal object of the invention is to provide a device that not only prevents the flow of blood from the corpora cavernosa, but is also minimally disruptive to the individual who must utilize the device. This objective is satisfied by use of the device of the present invention. Additionally, and of equal importance, a further objective is to provide a device which provides for cleanliness by providing a cost-efficient product that is disposable.

Such a device consists of a strip of interlocking material with the interlocking material exposed on both sides of the strip, such as, for example, VELCRO ®. A hoop, functioning as a "noose," is attached to one end of the device. Alternatively, a strip of cloth is attached to one end of the device to contact the skin of the penis. The resulting device, formed like a collar around the penis, is cinched as tightly as possible at the base of the penis by use of the noose located at one end of the device through which the other end is inserted and pulled. Alternatively, the user may hold the cloth with one hand and the VELCRO ® strip with the other, wrapping the cloth around the skin and continuing the wrapping of the interlocking portions of the strip to prevent slippage of the device during use.

The following drawings are set forth for illustrative purposes and are not to be construed as limiting or constricting the claims of the present invention in any manner.

BRIEF DESCRIPTION OF DRAWINGS

FIG. 1 is a top perspective view of one embodiment of the present invention.

FIG. 2 is a side view of the device of FIG. 1.

FIG. 3 is an end view of one embodiment of the present invention being applied to the base of the male genitalia.

FIG. 4 is an end view of one embodiment of the present invention applied to the base of the male genitalia.

DESCRIPTION OF THE PREFERRED EMBODIMENT

Figure 8:
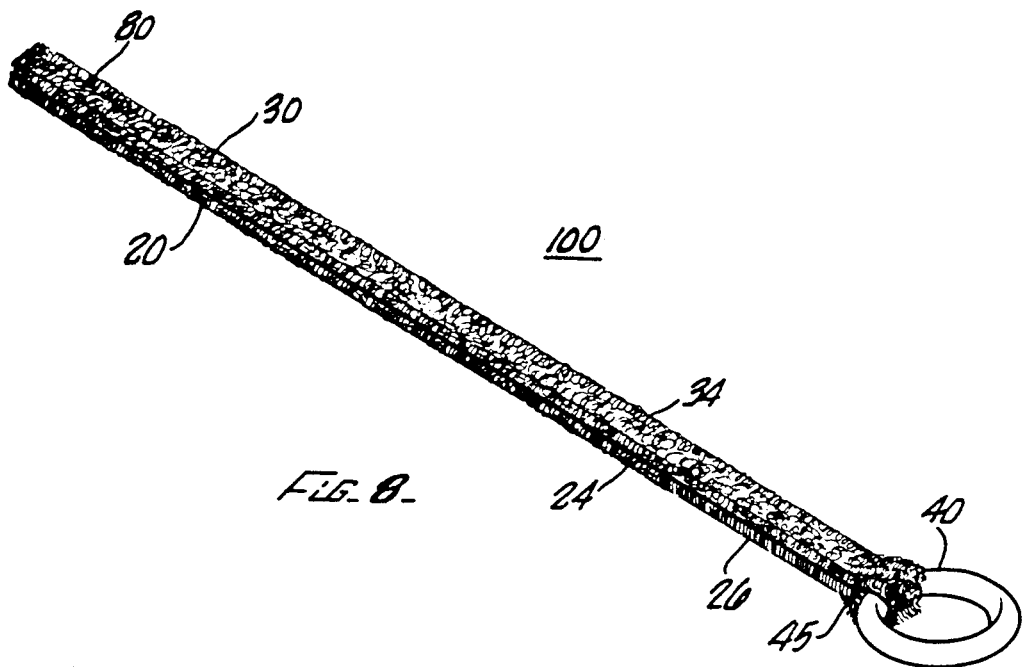
FIG. 8 is a top perspective view of the preferred embodiment of the present invention.
Figure 9:
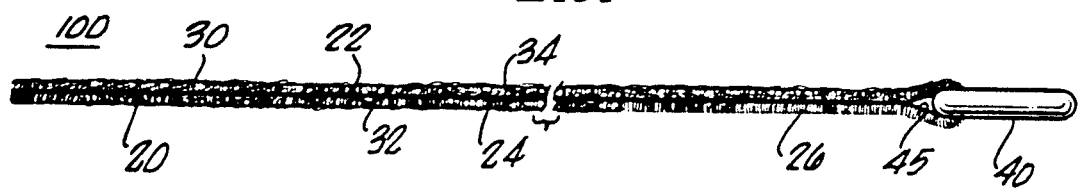
FIG. 9 is a side view of the device of FIG. 8.

The preferred embodiment of the present invention is depicted in FIGS. 8, 9, 10 and 11. As illustrated in FIG. 8 and FIG. 9, device 100 consists of two strips of an interlocking material, 20, 30, such as, and preferably, VELCRO ®, as this material is easily manipulated by the user and maintains a firm, self locking interaction, a necessity for restricting the back flow of blood from the corpora cavernosa during copulation. However, any material that will satisfy the objectives of the present invention can be utilized. Said strips are glued back to back, with a noose-like hoop 40 interconnected to said strips at junction 45 of said strips. A pressure sensitive adhesive 22 and 32 (FIG. 9) is coated on the back sides of strips 20 and 30, respectively; such adhesive holds said strips together. Hoop 40 is made of a non-deformable material, preferably a plastic, and should be smooth and have a generally circular configuration. Strip 20 measures approximately eight (8) inches in length by three-eighths ($\frac{3}{8}$) inch in width, having on the exposed side thereof a series of loops 24 extending approximately five and one half ($5\frac{1}{2}$) inches from the end opposite to hoop 40; the remaining two and one half ($2\frac{1}{2}$) inches consists of a series of hooks 26. Strip 30 measures approximately eight (8) inches in length by three-eighths ($\frac{3}{8}$) inch in width, having on the exposed side thereof a series of loops 34.

Figure 10:
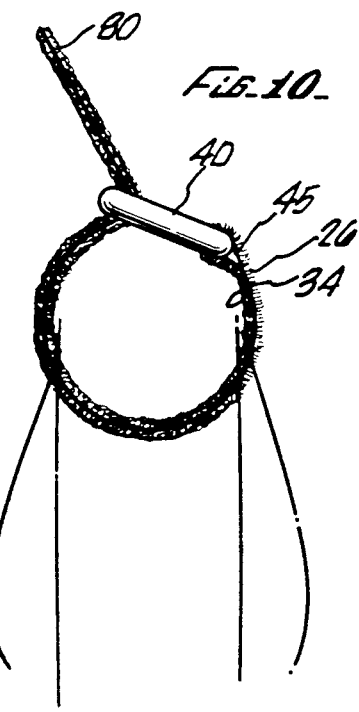
FIG. 10 is an end view of the preferred embodiment of the present invention being applied to the base of the male genitalia.
Figure 11:
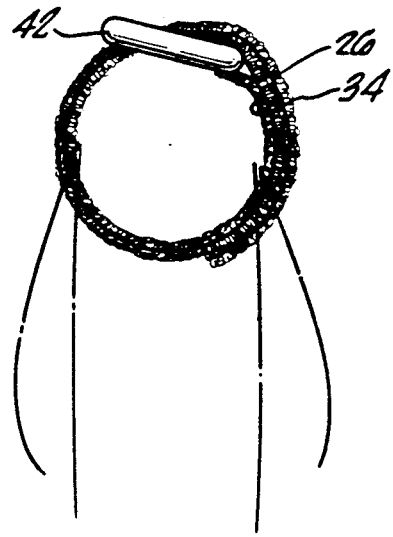
FIG. 11 is an end view of the preferred embodiment of the present invention applied to the base of the male genitalia.

As illustrated in FIG. 10, the device is applied as a collar around the base of the penis and scrotum at their junction with the pubis. Turning side 30 of the device toward the skin, a noose is formed by feeding end 80 through loop 40. The user then grabs base 45 of the device, and end 80 is pulled as tightly as possible by the user with the other hand. As illustrated in FIG. 11, the exposed hooks 26 on side 20 interconnect with loops 34 of the device. Thus, the device is held firmly in place.

In an alternative embodiment of the preferred embodiment of the present invention, as illustrated in FIGS. 1, 2, 3 and 4, and designated as 100a, hoop 40a is also made of two strips of an interlocking material glued back to back, each measuring three (3) inches by three-sixteenths (3/16) inch; one-half ($\frac{1}{2}$) inch of each end is embedded between strips 20a, 30a at junction 45a. Hoop 40a serves two purposes: first, to provide a means for cinching tightly the collar around the base of the penis, and second, to help hold the collar in place. Strips 20a, 30a and hoop 40a are preferably made of VELCRO ® for the previously stated reasons. Again, however, any material that will satisfy the objectives of the present invention can be utilized. The obverse sides of strips 20a and 30 are coated with a pressure sensitive adhesive layer, 25 and 35 (FIG. 2), respectively. The end portion 80a, opposite to that of hoop 40, is inserted through said hoop prior to and during use, as illustrated in FIG. 3 and FIG. 4.

As is depicted in FIG. 3, the device is applied in the same manner as the preferred embodiment; turning side 20a of the device toward the skin, a noose is formed by feeding end 80a through hoop 40a. Hoop 40a is then grasped at base 45a by the user, and end 80 is pulled as tightly as possible. As illustrated in FIG. 4, because hoop 40a is also preferably made of VELCRO ®, said hoop also helps to hold the device in place when the endpoint 42a of said hoop is pressed firmly against hooks 34a.

Figure 5:
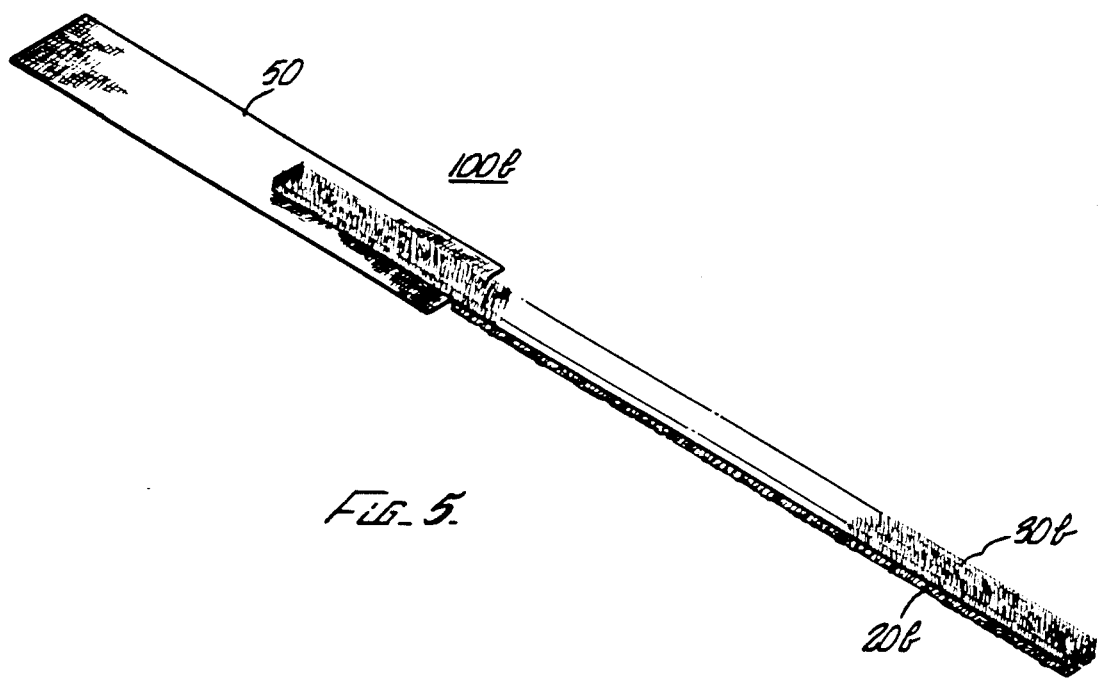
FIG. 5 is a top perspective view of another embodiment of the present invention.
Figure 6:
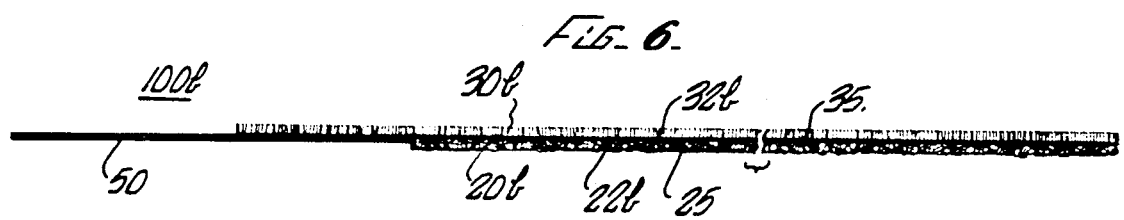
FIG. 6 is a side perspective view of the embodiment of FIG. 5.
Figure 7:
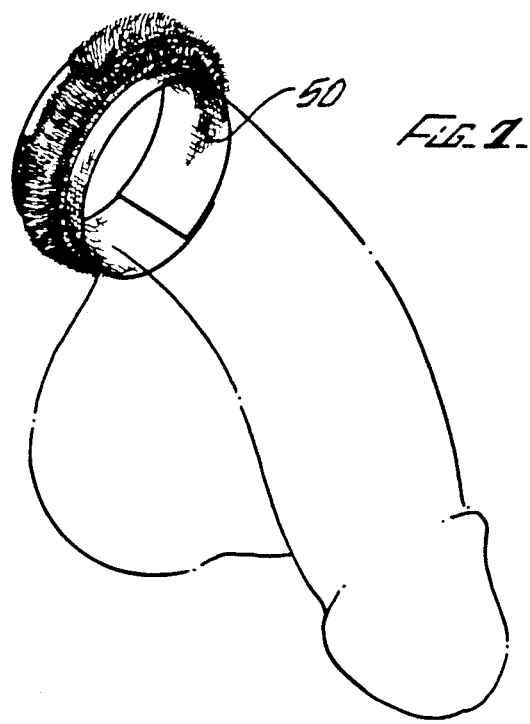
FIG. 7 is a perspective view of another embodiment of the present invention applied to the base of the male genitalia.

A further embodiment of the present invention is depicted in FIGS. 5, 6 and 7. As set forth in FIG. 5 and FIG. 6, device 100b consists of two strips of an interlocking material 20b, 30b glued back to back, and a strip of material 50 to which the human skin is not allergic, e.g., synthetic materials or natural materials. Material 50 is preferably a cotton or cotton-blend material. Strips 20b, 30b are also preferably made of VELCRO ®. Strip 20b measures approximately eight (8) inches by one and one-half ($1\frac{1}{2}$) inch, one side of which is covered with loops 22b and the obverse side is coated with a pressure sensitive adhesive 25b. Strip 30b measures approximately six and three-quarter ($6\frac{3}{4}$) inches by one-half ($\frac{1}{2}$) inch, one side of which is covered with hooks 32b and the obverse side is also covered with pressure sensitive adhesive 35b. Attached to the adhesive portion 35b is a three and one-half ($3\frac{1}{2}$) by three-quarter ($\frac{3}{4}$) inch length of material 50 which abuts the end of strip 20b.

As illustrated in FIG. 7, material 50 is in contact with the skin. By holding material 50 with one hand, and holding device 100b with the other, the user can tightly cinch the device around the base of the penis and securely fashion the collar thereon by pressing the interconnecting portions (22b and 32b) of said strips against one another.

The present device provides maximum success if applied before penial tumescence occurs. Furthermore, the device does not constrict the urethra and therefore will not interfere with normal ejaculation. The device is also easily removed after copulation. Because the device is not large and bulky, and because it is manufactured of relatively inexpensive materials, the present invention is not prohibitively expensive. Accordingly, the device described herein can be safely disposed after it is used, which increases the sanitary utility of the device.

While the invention has been described and illustrated with respect to specific embodiments, it is to be understood that modifications and equivalents thereof may be apparent to those skilled in the art and are intended to be within the scope of the invention.

I claim:
1. A method for maintaining erection of the penis during copulation comprising the steps of:
    encircling the base of the penis and scrotum at the junction of the pubis prior to penial tumescence with a device comprising: a single band of material being at least of a length sufficient to both encircle the base of the penis and scrotum at the junction of the pubis in one circle and having portions comprised of an interlocking material to interconnect against itself when so encircled, and further including a loop extending from an end of said interlocking material;
    pulling an end of said device through said loop;
    cinching the one circle of said band of the device as tightly as possible against said junction; and
    interconnecting said band against itself for maintaining the tightly cinched one circle of said band around said junction.
2. The method of claim 1 wherein said loop is an interlocking material.
3. The method of claim 1 or 2 wherein said interlocking material is VELCRO ®.
4. The method of claim 1 wherein said loop is a plastic material.
5. A method for maintaining erection of the penis during copulation comprising the steps of:
    encircling the base of the penis and scrotum at the junction of the pubis prior to penial tumescence with a device comprising: a band of interlocking material being at least of a length sufficient to both encircle the base of the penis and scrotum at the junction of the pubis and interconnect against itself when so encircled, and a swatch of material extending from one end of said band of interlocking material, said swatch being of sufficient length to encircle the base of the penis and scrotum at the junction of said pubis;

placing said swatch against the skin of said penis;

wrapping said swatch around said junction;

cinching as tightly as possible said swatch against said skin; and interconnecting the band of said device against itself around said swatch.

6. The method of claim 5 wherein said interlocking material is VELCRO ®.

7. The therapeutic device of claim 5 wherein said swatch is a material to which the human skin is not allergic.

8. The therapeutic device of claim 7 wherein said material is a synthetic material.

9. The therapeutic device of claim 7 wherein said material is a natural material.

10. The therapeutic device of claim 9 wherein said material is cotton.

11. A therapeutic device for maintaining erection of the penis during copulation comprising; a swatch of material of a sufficient length for encircling the base of the penis and scrotum at the junction of the pubis prior to penial tumescence, and a band of interlocking material connected to said swatch and extending from one end of said swatch, said band having a length at least sufficient to both encircle the base of the penis and scrotum at the junction of the pubis and interconnect against itself when so encircled, said swatch being adapted to be placed against the skin of the penis and scrotum at the junction and cinched tightly by interconnecting the band of said device against itself around said swatch.

12. The therapeutic device of claim 11 wherein said interlocking material is VELCRO ®.

13. The therapeutic device of claim 11, wherein said swatch is a material to which the human skin normally is not allergic.

14. The therapeutic device of claim 12, wherein said material is a synthetic material.

15. The therapeutic device of claim 12, wherein said material is a natural material.

16. The therapeutic device of claim 14, wherein said material is cotton.

* * * * *